United States Patent
Babkin et al.

(10) Patent No.: US 8,740,892 B2
(45) Date of Patent: Jun. 3, 2014

(54) EXPANDABLE MULTI-TUBULAR CRYOPROBE

(75) Inventors: Alexei V. Babkin, Albuquerque, NM (US); Anatoly I. Efremov, Albuquerque, NM (US); Jay J. Eum, Irvine, CA (US)

(73) Assignee: Endocare, Inc., Austin, TX (US)

( * ) Notice: Subject to any disclaimer, the term of this patent is extended or adjusted under 35 U.S.C. 154(b) by 1048 days.

(21) Appl. No.: 12/744,033

(22) PCT Filed: Nov. 19, 2008

(86) PCT No.: PCT/US2008/084040
§ 371 (c)(1),
(2), (4) Date: Jul. 29, 2010

(87) PCT Pub. No.: WO2009/067517
PCT Pub. Date: May 28, 2009

(65) Prior Publication Data
US 2011/0009854 A1    Jan. 13, 2011

Related U.S. Application Data

(60) Provisional application No. 60/989,776, filed on Nov. 21, 2007.

(51) Int. Cl.
*A61B 18/18* (2006.01)
(52) U.S. Cl.
USPC .............. 606/23; 606/20; 606/21; 606/22
(58) Field of Classification Search
USPC ................................. 606/20–26
See application file for complete search history.

(56) References Cited

U.S. PATENT DOCUMENTS

| | | | |
|---|---|---|---|
| 5,037,395 A | 8/1991 | Spencer | |
| 5,108,390 A | 4/1992 | Potocky | |
| 5,400,602 A | 3/1995 | Chang | |
| 5,520,682 A | 5/1996 | Baust | |
| 5,573,532 A | 11/1996 | Chang | |
| 5,957,963 A | 9/1999 | Dobak | |
| 6,106,518 A * | 8/2000 | Wittenberger et al. | 606/23 |
| 6,161,543 A | 12/2000 | Cox | |
| 6,241,722 B1 | 6/2001 | Dobak | |
| 6,355,029 B1 | 3/2002 | Joye | |

(Continued)

FOREIGN PATENT DOCUMENTS

WO    WO2005/063136    7/2005

OTHER PUBLICATIONS

Gage AA, Baust J; Mechanisms of Tissue Injury in Cryosurgery; Cryobiology 37; (1998) 171-186; Article CY982115; Academic Press.

(Continued)

*Primary Examiner* — Linda Dvorak
*Assistant Examiner* — Jaymi Della
(74) *Attorney, Agent, or Firm* — Lawrence N. Ginsberg (57) ABSTRACT

An expandable, flexible multi-tubular cryoprobe operational with a near critical cryogenic working fluid. The inlet fluid transfer micro-tubes utilized are formed of material that maintains flexibility in a full range of temperatures from −200° C. to ambient temperature. During operation, the cryoprobe is mechanically actuated to provide radial expansion of the inlet fluid transfer micro-tubes. Thus, enhanced thermal contact with target biological tissue to be treated is provided.

9 Claims, 5 Drawing Sheets

(56) References Cited

U.S. PATENT DOCUMENTS

| | | |
|---|---|---|
| 6,537,271 B1 | 3/2003 | Murray |
| 6,551,309 B1 | 4/2003 | LiPivert |
| 6,685,720 B1 | 2/2004 | Wu |
| 6,726,653 B2 | 4/2004 | Noda |
| 6,767,346 B2 | 7/2004 | Damasco |
| 6,893,419 B2 | 5/2005 | Noda |
| 6,893,433 B2 | 5/2005 | Lentz |
| 6,936,045 B2 | 8/2005 | Yu |
| 6,989,009 B2 | 1/2006 | Lafontaine |
| 7,022,120 B2 | 4/2006 | Lafontaine |
| 7,083,612 B2 | 8/2006 | Littrup |
| 7,220,252 B2 | 5/2007 | Shah |
| 7,220,257 B1 | 5/2007 | Lafontaine |
| 7,273,479 B2 | 9/2007 | Littrup |
| 7,410,484 B2 | 8/2008 | Littrup |
| 2001/0047134 A1 | 11/2001 | Holdaway |
| 2002/0049409 A1* | 4/2002 | Noda et al. .................... 604/113 |
| 2003/0055415 A1* | 3/2003 | Yu et al. ......................... 606/21 |
| 2004/0148004 A1 | 7/2004 | Wallsten |
| 2005/0209587 A1 | 9/2005 | Joye |
| 2006/0212027 A1* | 9/2006 | Marrouche et al. ............. 606/21 |
| 2006/0212028 A1 | 9/2006 | Joye |
| 2006/0235375 A1* | 10/2006 | Littrup et al. .................. 606/21 |
| 2006/0247611 A1 | 11/2006 | Abboud |
| 2006/0253114 A1 | 11/2006 | Saadat |
| 2007/0005077 A1* | 1/2007 | Null et al. ..................... 606/104 |

OTHER PUBLICATIONS

Hoffmann NE, Bischof JC; The Cryobiology of Cryosurgical Injury; Urology 60; (2002) 40-49; Elsevier Science Inc.

Gage AA, Baust J.: Mechanisms of tissue injury in cryosurgery. Cryobiology. 1998;37:171-186; and, Hoffmann NE, Bischof JC: The cryobiology of cryosurgical injury. Urology 2002;60;40-49.

International Application No. PCT/US2008/084040 International Search Report and Written Opinion Dated Feb. 3, 2009 Attached to International Publication No. WO2009/067517.

Supplementary Partial European Search Report Regarding Application No. EP08852762 Dated Nov. 18, 2010.

* cited by examiner

FIG. 12

EXPANDABLE MULTI-TUBULAR CRYOPROBE

CROSS REFERENCE TO RELATED APPLICATIONS

This application is a national stage of International Application No. PCT/US2008/084040, filed Nov. 19, 2008, which claims the benefit of U.S. Provisional Application Ser. No. 60/989,776, filed Nov. 21, 2007. The entire contents of each application are hereby incorporated herein by reference in their entirety.

BACKGROUND OF THE INVENTION

1. Field of the Invention

The present invention relates to cryotherapy devices and more particularly to an expandable multi-tubular cryoprobe for freezing and destroying biological tissues.

2. Description of the Related Art

Cryosurgical therapy involves the application of extremely low temperature and complex systems designed to suitably freeze the target biological tissue to be treated. Many of these systems use cryoprobes with particular shapes and sizes that are designed to contact a selected portion of the tissue without undesirably effecting adjacent healthy tissues or organs. Extreme freezing is produced with refrigerants that are introduced through a flexible or rigid probe. The freezing is then applied to the target tissue through a heat transfer element formed as a part of the probe and limited to applying the freezing to a relatively small location.

Typically the heat transfer element is positioned at a distal end of the probe. It must be small enough to permit its easy introduction into the treatment area, but, must also provide a tight thermal contact with target tissue, i.e., it must be large enough to contact all the target tissue directly thereby allowing the freezing of all the target tissue in one step.

To realize tight thermal contact between the heat transfer element and the target tissue the distal end of the cryoprobe is conventionally designed with a small balloon that is positioned in the selected location and is then inflated to contact the target tissue, such as the wall of a blood vessel. This inflation may be achieved by expanding a compressed refrigerant into the balloon. Alternatively, it may be achieved by introducing a separate pressurized fluid through the probe into the balloon.

Known cryosurgical devices using inflated balloons are described in U.S. Pat. No. 6,355,029, issued to Joye, et al, entitled, "Apparatus and Method for Cryogenic Inhibition of Hyperplasia"; U.S. Pat. No. 6,537,271, issued to Murray, et al, entitled, "Balloon Cryogenic Catheter"; U.S. Pat. No. 6,685,720, issued to Wu, et al, entitled "Catheter Having Improved Shaped Retention"; U.S. Pat. No. 6,893,433, issued to Lentz, entitled "System and Method for Performing a Single Step Cryoablation"; U.S. Pat. No. 7,022,120, issued to LaFontaine, entitled "Cryoplasty Device and Method"; U.S. Pat. No. 7,220,252, issued to Shah, entitled "Inflatable Dual Balloon Catheter"; WIPO Pub. No. 2005/063136 A2, to Vancelette, et al, entitled "Cryosurgical Devices and Methods for Endometrial Ablation"; U.S. Pub. No. 2004/0148004, to Wallsten, entitled, "Balloon Catheter and Method for Treatment of a Mammalian Duct or Cavity by Pressure or Heat"; U.S. Pub. No. 2006/0212028, issued to Joye, et al, entitled, "Cryosurgical Fluid Supply"; U.S. Pub. No. 2006/0247611, issued to Abboud, et al, entitled "Wide Area Ablation of Myocardial Tissue'; and U.S. Pub. No. 2006/0253114, issued to Saadat, entitled "Methods and Apparatus for Cryo-Therapy".

U.S. Pub. No. 2006/0247611, issued to Abboud, et al, entitled "Wide Area Ablation Of Myocardial Tissue", discloses a distal end of the cryoprobe which is axially movable by means of a pull wire that simultaneously deforms a flexible element connected to an inflatable balloon that can expand radially from an initial diameter to a final diameter that is at least twice the initial diameter. The twice initial diameter of the inflatable balloon is relatively small to provide a reliable ablation surface. A common disadvantage of the prior art is the use of inflatable balloons that operate under internal pressure and a commensurate risk of sudden destruction and resultant injuring of the biological tissue to be treated.

SUMMARY

In a broad aspect the present invention is embodied as an expandable, flexible multi-tubular cryoprobe. The cryoprobe includes a housing for receiving an inlet flow of near critical cryogenic fluid from a fluid source and for discharging an outlet flow of the cryogenic fluid. An outer support tube is connected to the housing. A set of radially spaced inlet fluid transfer tubes have proximal ends securely attached to an inner surface of the outer support tube. The inlet fluid transfer tubes receive the inlet flow from the housing. Each of the fluid transfer tubes is formed of material that maintains flexibility in a full range of temperatures from −200° C. to ambient temperature, each fluid transfer tube having an inside diameter in a range of between about 0.10 mm and 1.0 mm. Furthermore, each fluid transfer tube has a wall thickness in a range of between about 0.01 mm and 0.30 mm. A proximal internal support tube is attached to the outer support tube and to internal surfaces of the proximal ends of the inlet fluid transfer tubes, thus forming a hollow space to provide a thermal insulation between the outer support tube and the inlet fluid transfer tubes. An outlet fluid transfer tube is positioned within the proximal internal support tube. The outlet fluid transfer tube is axially positionable and rotatable relative to the proximal internal support tube, the outlet fluid transfer tube for discharging the outlet flow to the housing. A distal external end cap is positioned at the ends of the inlet fluid transfer tubes and about the distal end of the outlet fluid transfer tube to provide fluid transfer from the inlet fluid transfer tubes to the outlet fluid transfer tube wherein a closed hollow space is formed between the end cap and the distal end of the outlet fluid transfer tube to provide fluid transfer from the distal ends of the inlet fluid transfer tubes to the distal end of the outlet fluid transfer tube. An open portion of the inlet fluid transfer tubes is located between the outer support tube and the distal external end cap. Mechanical means is operatively associated with the outlet fluid transfer tube for providing axial displacement of the distal external end cap relative to the outer support tube wherein, decreasing the distance therebetween results in radial expansion of the inlet fluid transfer tubes to provide enhanced thermal contact thereof with target biological tissue to be treated at the open portion.

DETAILED DESCRIPTION OF THE INVENTION

Figure 1:
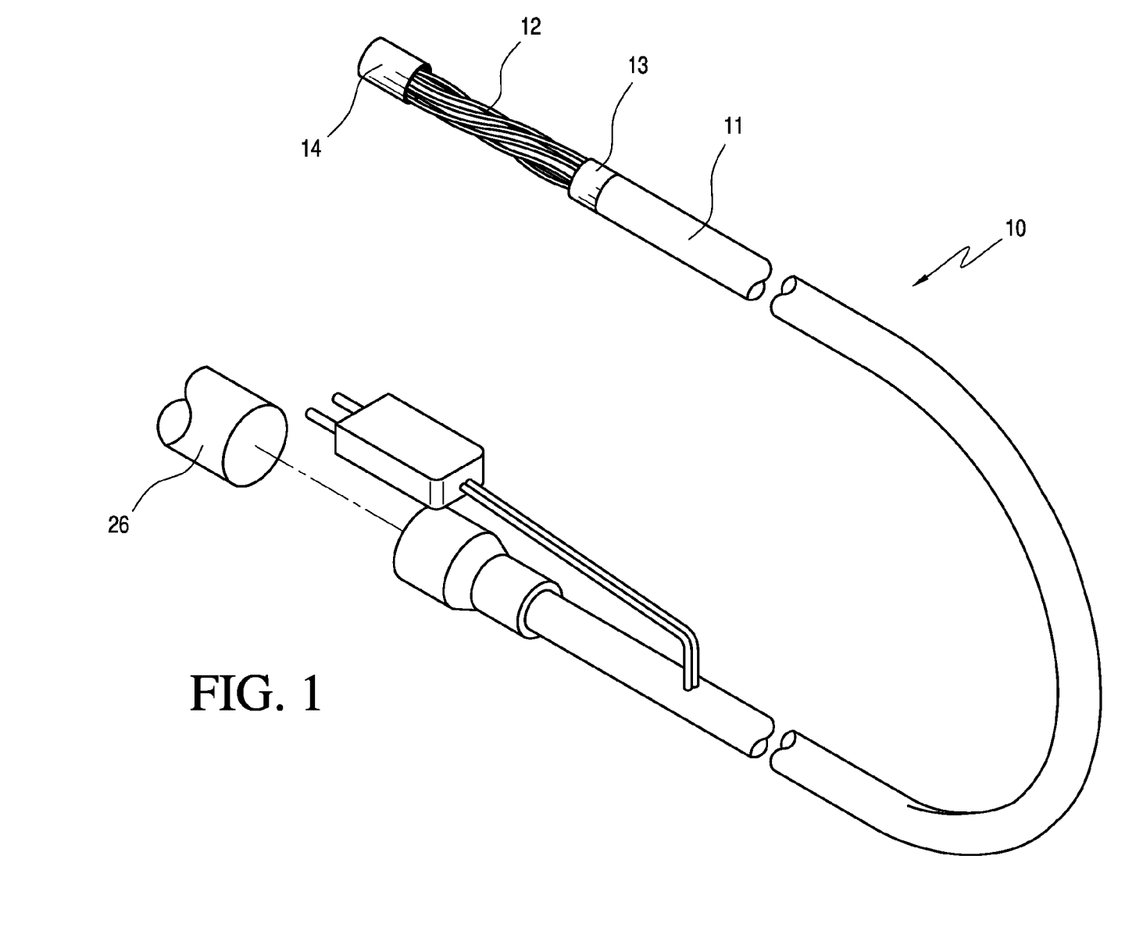
FIG. 1 is perspective view of the expandable, flexible multi-tubular cryoprobe of the present invention.

Referring now to the drawings and the characters of reference market thereon, FIG. 1 illustrates a preferred embodiment of the expandable, flexible multi-tubular cryoprobe of the present invention, designated generally as 10. The cryoprobe 10 includes a housing 11 containing a set of inlet fluid transfer tubes 12 for receiving an inlet flow of near critical cryogenic fluid from a liquid source 26 and for discharging an outlet flow of the cryogenic fluid through a central outlet fluid transfer tube (discussed below). The cryoprobe 10 includes an outer support tube 13 connected to the housing 11. The set of radially spaced inlet fluid transfer tubes (or micro-tubes) 12 have proximal ends securely attached to an inner surface of the outer support tube 13. Each of the fluid transfer tubes 12 are formed of material that maintains flexibility in a full range of temperature from −200° C. to ambient temperature. Each fluid transfer tube 12 has an inside diameter in a range of between about 0.10 mm and 1.0 mm (preferably between about 0.20 mm and 0.50 mm) and wall thickness in a range of between about 0.01 mm and 0.3 mm (preferably between about 0.02 mm and 0.1 mm). An end cap 14 is positioned at the distal ends of the inlet fluid transfer tubes 12 to provide fluid transfer from the inlet fluid transfer tubes 12 to the outlet fluid transfer tube located inside the multi-tubular cryoprobe 10. The inlet fluid transfer tubes 12 are preferably formed of polyimide material, such as KAPTON® polyimide material.

The outer support tube 13 is preferably formed of annealed stainless steel or a polyimide, preferably KAPTON® polyimide material. It is necessary that the material maintains flexibility at a near critical temperature of cryogenic fluid.

As used herein the term "flexibility" refers to the ability of the cryoprobe to be bent in the orientation desired by the user without applying excess force and without fracturing or resulting in significant performance degradation.

The cryogenic fluid utilized is preferably near critical nitrogen. However, other near critical cryogenic fluids may be utilized such as argon, neon, or helium. As used herein, the term "near critical" refers to the liquid-vapor critical point. Use of this term is equivalent to the phrase "near a critical point" and it is the region where the liquid-vapor system is adequately close to the critical point, where the dynamic viscosity of the fluid is close to that of a normal gas and much less than that of the liquid; yet, at the same time its density is close to that of a normal liquid state. The thermal capacity of the near critical fluid is even greater than that of its liquid phase. The combination of gas-like viscosity, liquid-like density and very large thermal capacity makes it a very efficient coolant agent. In other words, reference to a near critical point refers to the region where the liquid-vapor system is adequately close to the critical point so that fluctuations of the liquid and vapor phase are large enough to create a large enhancement of the heat capacity over its background value. As used herein, the term near critical temperature refers to a temperature within ±10% of the critical point temperature. The near critical pressure is between 0.8 and 1.2 times the critical pressure.

The fluid source for the cryogenic fluid may be provided from a suitable mechanical pump or a non-mechanical critical cryogen generator. Such fluid sources are disclosed in, for example, U.S. patent application Ser. No. 10/757,768 which issued as U.S. Pat. No. 7,410,484, on Aug. 12, 2008 entitled "CRYOTHERAPY PROBE", filed Jan. 14, 2004 by Peter J. Littrup et al.; U.S. patent application Ser. No. 10/757,769 which issued as U.S. Pat. No. 7,083,612 on Aug. 1, 2006, entitled "CRYOTHERAPY SYSTEM", filed Jan. 14, 2004 by Peter J. Littrup et al.; U.S. patent application Ser. No. 10/952,531 which issued as U.S. Pat. No. 7,273,479 on Sep. 25, 2007 entitled "METHODS AND SYSTEMS FOR CRYOGENIC COOLING" filed Sep. 27, 2004 by Peter J. Littrup et al. U.S. Pat. No. 7,410,484, U.S. Pat. No. 7,083,612 and U.S. Pat. No. 7,273,479 are incorporated herein by reference, in their entireties, for all purposes.

Referring now to FIGS. 2-5 it can be seen that the cryoprobe 10 includes the outer support tube 13 attached to internal surfaces of the proximal ends of the inlet fluid transfer tubes 12. The inlet fluid transfer tubes 12 are uniformly distributed and rigidly fixed around the outer surface of a proximal internal tube 15 having length of fixation $L_1$. (The tubes 12 are illustrated in these figures as being twisted; however, they may be initially straight.) The distal ends of the inlet fluid transfer tubes 12 are rigidly fixed with the end cap 14 and the outer surface of central outlet fluid transfer tube 16 having a length of fixation $L_2$. The proximal outer support tube 13, being rigidly fixed with the inlet fluid transfer tubes 12 and the outer surface of the proximal internal tube 15 on the length of fixation $L_1$, forms a vacuum space of insulation 17. The outlet fluid transfer tube 16 can freely rotate and move axially inside the proximal internal support tube 15. The proximal internal support tube 15 is rigidly fixed with the outer support tube 13 and inlet fluid transfer micro-tubes 12 with a length of fixation $L_1$. The hollow space 17 between the proximal internal support tube 15 and outer support tube 13 is a space of vacuum thermal insulation. The end cap 14, being rigidly fixed with parallel filaments of inlet fluid transfer tubes 12 and central outlet fluid transfer tube 16 on the length $L_2$, forms a closed hollow space 18 to provide closed direct fluid transfer from the inlet fluid transfer tubes 12 to the central outlet fluid transfer tube 16, as shown by the arrows. The inlet fluid transfer tubes 12 form a deformable open portion that defines a cooling area on the length $L_3$. This open portion is intended to provide a tight thermal contact between deformed inlet fluid transfer tubes 12 and biological tissue to be treated. The central outlet fluid transfer tube 16 discharges the outlet flow to the housing 11. Mechanical means is operatively associated with central outlet fluid transfer tube 16 for providing axial displacement of the end cap 14 relative to the outer support tube 13. The mechanical means preferably also provides relative rotation of the transfer tube 16 and the end cap 14 about longitudinal axis C-C. The mechanical means may be, for example, conventional means including hand manipulation. A possible mechanical means may comprise use of an electrically powered drive to rotate the outlet fluid transfer tube 16 and end cap 14 in combination with an axial spring to realize its axial displacement. Magnetic forces may also be utilized.

Figure 5:
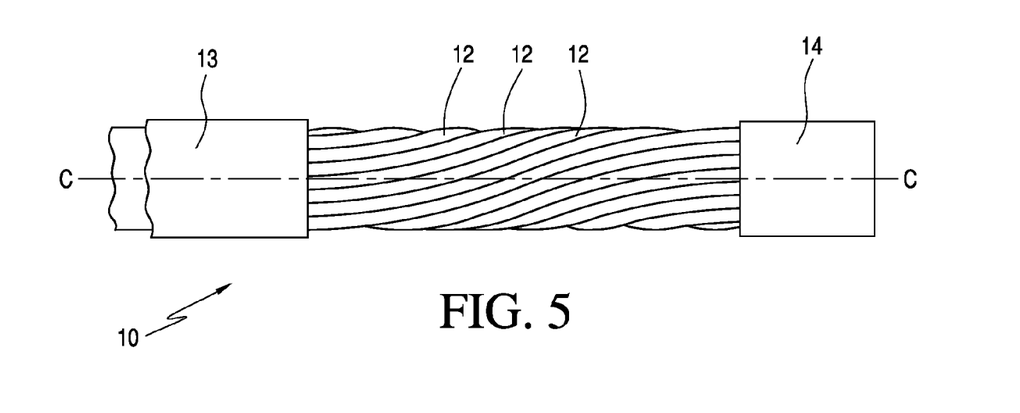
FIG. 5 is a side view of the distal end of the cryoprobe in an unexpanded spiral state.

In the first step of an operational procedure the central outlet fluid transfer tube 16 that is rigidly fixed with the distal ends of the inlet fluid transfer tubes 12 and end cap 14 rotates around the longitudinal axis C-C to form a spiral shape of inlet fluid transfer tubes 12 on the open portion shown in FIG. 5. In this unexpanded spiral state, the diameter formed by the inlet fluid transfer tubes 12 is slightly less than the diameter of the outer support tube 13 and end cap 14. This position corresponds to operational insertion of the multi-tubular cryoprobe into the treatment area close to target tissue.

Figure 6:
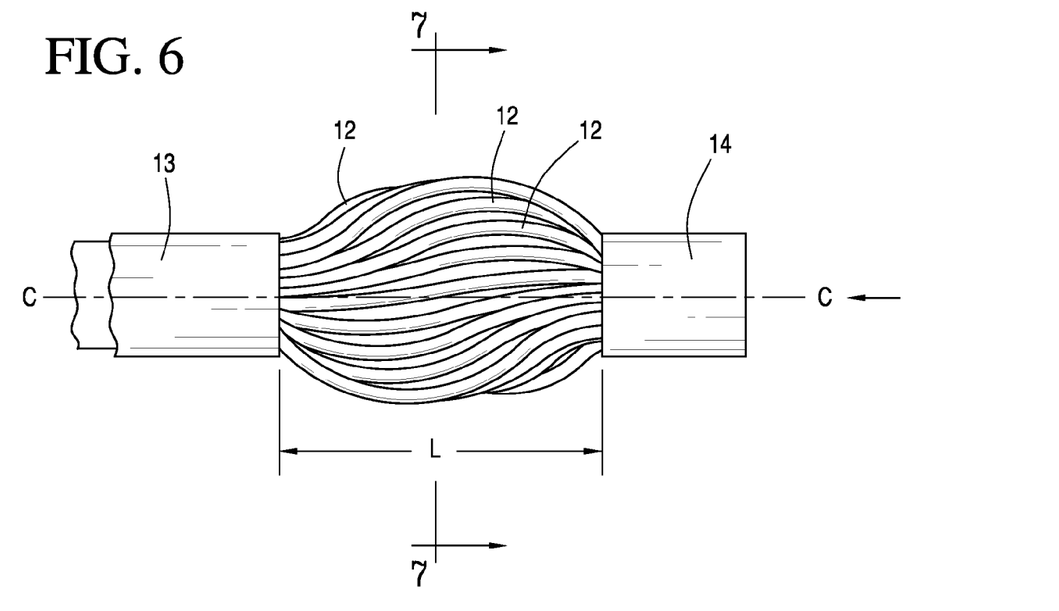
FIG. 6 is a side view of the distal end of the cryoprobe in an expanded spiral state.
Figure 7:
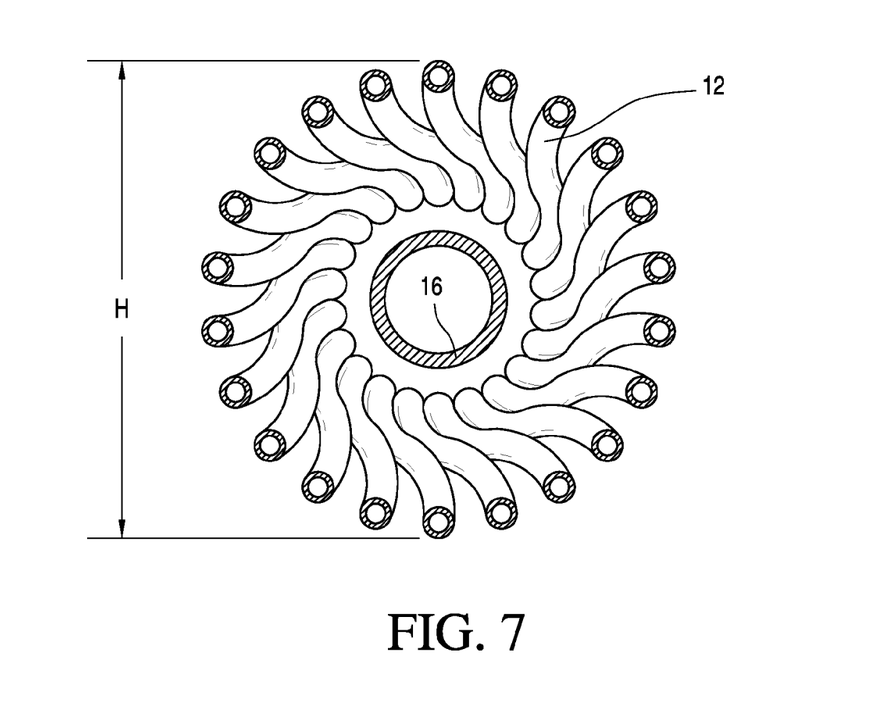
FIG. 7 is a view taken along line 7-7 of FIG. 6.

Referring now to FIGS. 6 and 7, in the next step of the operational procedure, the central outlet fluid transfer tube 16, that is rigidly connected with end cap 14 and spirally wound inlet fluid transfer tubes 12, has moved axially inwardly relative to the proximal outer support tube 13, thus expanding the effective diameter of the inlet fluid transfer tubes 12. This expanded set of spiral filaments of inlet fluid transfer tubes 12 provides tight contact with target tissue to be cooled and enhanced thermal conductivity.

Figure 8:
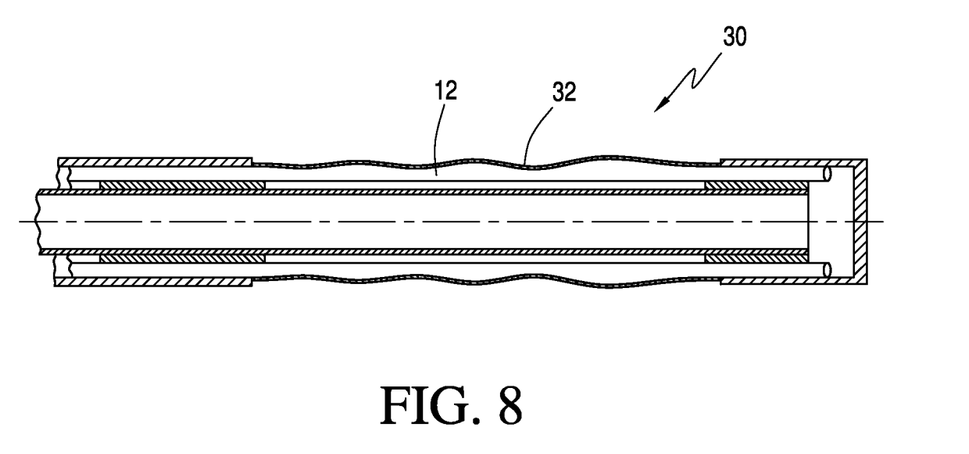
FIG. 8 is a cross-sectional view of the distal end of an alternate type of cryoprobe with a thin outer layer/balloon over the inlet fluid transfer tubes.

Referring now to FIG. 8, an alternate embodiment of the cryoprobe is illustrated, designated generally as 30. In this embodiment, a thin elastic shell 32 is provided over the open portion of inlet fluid transfer tubes 12. A vacuum pump can be used to draw some negative pressure which will insure good contact between tubes 12 and the outside shell 32. Additionally, this minimizes the potential for leakage and allows detection of unlikely but possible leakage from the tubes 12. When pressure inside the shell 32 rises, the system immediately stops flow of cryogenic fluid and draws more vacuum from this shell. The elastic shell 32 also provides enhanced thermal conductivity.

EXAMPLE

In an exemplary embodiment of the invention shown in FIGS. 2-7 the central outlet fluid transfer tube 16 is manufactured from heavy wall stainless steel tube HTX-18× with OD=0.05" and ID=0.03". This tube is inserted into the internal tube 15, manufactured from standard polyimide tube TWPT-057 with OD=0.0646" and ID=0.0571". The set of parallel inlet fluid transfer micro-tubes 12 are manufactured from standard polyimide tube SWPT-008 with OD=0.0104" and ID=0.0089" having relatively high allowable internal pressure of about 1854 psi. The set of micro-tubes 12 is rigidly fixed on outer surface of the internal polyimide tube 15. The micro-tubes 12 have a length of fixation $L_1=0.3"$. The number "n" of micro-tubes 12 is equal to:

$$n=L_0/0.0104",$$

where $L_0=\pi D$ is a full length of the circumference formed by outer diameter of TWPT-57 internal polyimide tube and outer diameter of inlet fluid transfer tube SWPT-008. The diameter of the circumference will be:

$$D=(0.0646"+0.0104")=0.075",$$

so the number of inlet fluid transfer micro-tubes 12 will be:

$$n=3.14\times0.075"/0.0104"\sim22.$$

Figure 2:
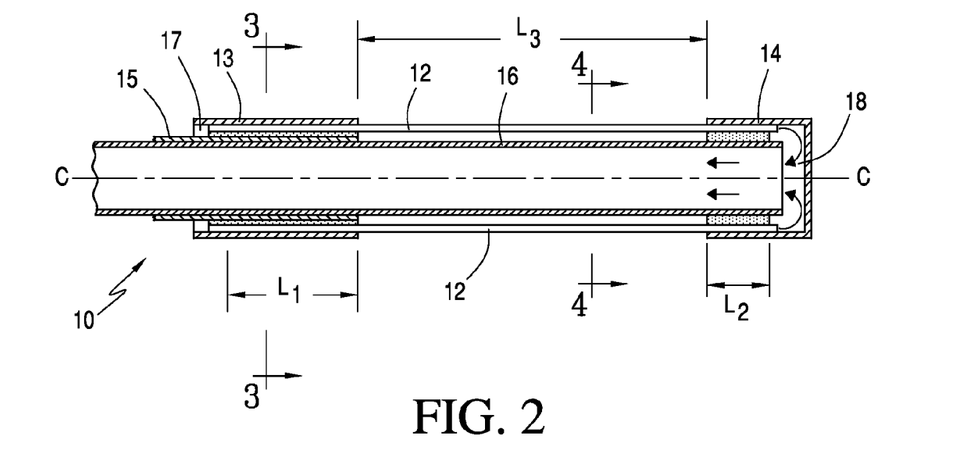
FIG. 2 is a cross-sectional view of the distal end of the cryoprobe of FIG. 1.
Figure 3:
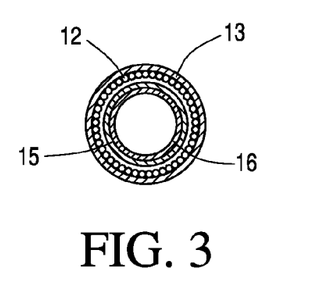
FIG. 3 is a view taken along line 3-3 of FIG. 2.
Figure 4:
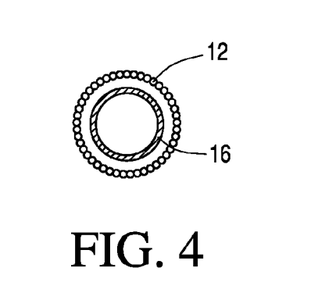
FIG. 4 is a view taken along line 4-4 of FIG. 2.

The outer support tube 13, manufactured from thin wall stainless steel tube HTX-12T with OD=0.109" and ID=0.091", envelops the left (proximal) part of the micro-tubes 12. It is rigidly fixed with the set n=22 of the micro-tubes 12 on a length of fixation $L_1=0.3"$. The proximal support tube 13 is thermally insulated from the set of inlet fluid transfer micro-tubes 12 by means of vacuum space 17.

The blind end cap 14 is manufactured from the same thin wall stainless tube HTX-12T. It envelops the right (distal) part of the set n=22 of inlet fluid transfer micro-tubes 12. The blind end cap 14 and distal end of central outlet fluid transfer tube 16 are rigidly connected with distal end of inlet fluid transfer micro-tubes 12 on a length $L_2=0.3"$ forming a closed hollow space 18 to provide closed direct fluid transfer from inlet fluid transfer micro-tubes 12 to the central outlet fluid transfer tube 16. The inlet fluid transfer micro-tubes 12 have a deformable open portion on a length $L_3=1.5"$ intended to provide an operational thermal contact of micro-tubes 12 with the target tissue to be cooled (not shown). The central outlet fluid transfer tube 16 that is rigidly connected with the end cap 14 and inlet fluid transfer micro-tubes 12 rotates around the longitudinal axis C-C forming a spiral shape of the set of inlet fluid transfer micro-tubes 12 shown in FIG. 5. This movement corresponds to the first step of operational procedure.

The second movement of operational procedure shown in FIGS. 6 and 7 with an arrow includes axial displacement of the central outlet fluid transfer tube 16 relative to the end cap 14 providing transversal expansion H of spiral shaped micro-tubes 12 located in deformable open portion having a final operational length L.

Figure 9:
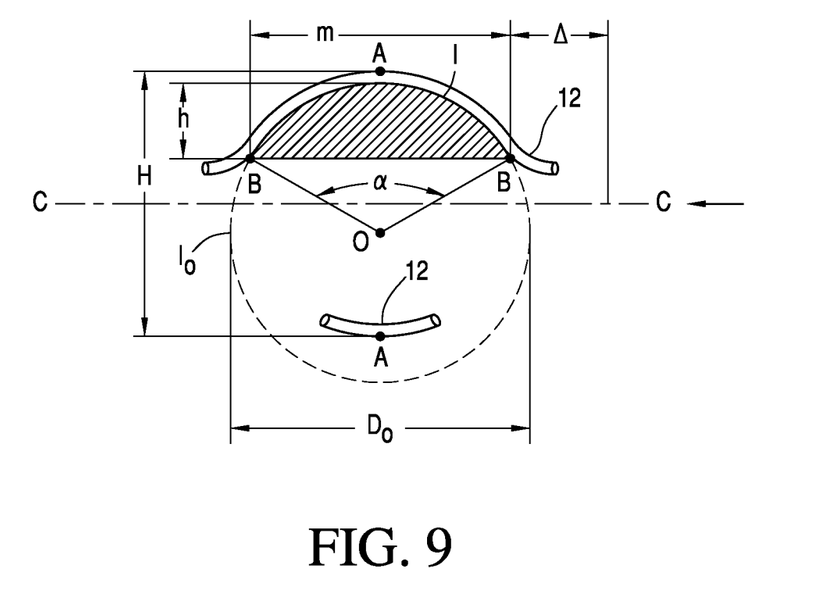
FIG. 9 is a schematic illustration of the radial expansion of the inlet fluid transfer tube.

FIG. 9 illustrates an expansion process when, for example, the inlet fluid transfer tube 12 is deformed by axial displacement $\Delta$ of the outlet fluid transfer tube forming ⅓ part of the circle with center O. A circular line B-B has a length l=1.3". In this case the full length $l_0$ of the circle with center O will be:

$$l_0=3l=3\times1.3"=3.9",$$

that corresponds to diameter $D_0$ of the circle that is equal to:

$$D_0=l_0/\pi=3.9"/3.14=1.24".$$

The area S of shaded circular segment may be calculated with following formulas:

$$S=D_0^2(\pi\alpha/180°-\sin\alpha)/8, \quad (1)$$

or $$S=[D_0(l-m)/2+mh]/2, \quad (2)$$

where $\alpha=120°$, h is a height of the circular segment, and m is a length of the chord as shown in FIG. 9.

The area S calculated with formula (1) is:

$$S=(1.24")^2(3.14\times120°/180°-\sin 120°)/8=0.24 \text{ sq. in.}$$

The length of the chord is equal to:

$$m=D_0\sin(180°/3)=1.24"\times\sin 60°=1.24\times0.87=1.08",$$

and the height h of the circular segment will be calculated from formula (2) as:

$$h=[2S-D_0(l-m)/2]/m=[2\times0.24-1.24"(1.3"-1.08")/2]/1.08"=0.32".$$

Full elevation of the highest points A-A of the set of inlet fluid transfer tubes 12 will be:

$$H=2(0.32"+0.0104"+0.0646"/2)=0.725",$$

This is 0.725"/(0.0646+2×0.0104)=8.5 times greater than diameter of the open portion of the distal end.

The axial displacement $\Delta$ of the distal end is only:

$$\Delta=l-m=1.3"-1.08"=0.22".$$

It is evident that the size and dimensions of the distal end may vary depending on specific multi-tubular cryoprobe application.

In addition to having a high radial expansion the present invention allows for relatively high internal pressure inside the tubes 12 defined by the standard polyimide tubes to be used. With these features the present invention is characterized by extreme reliability and effective cryosurgical operation.

Figure 10:
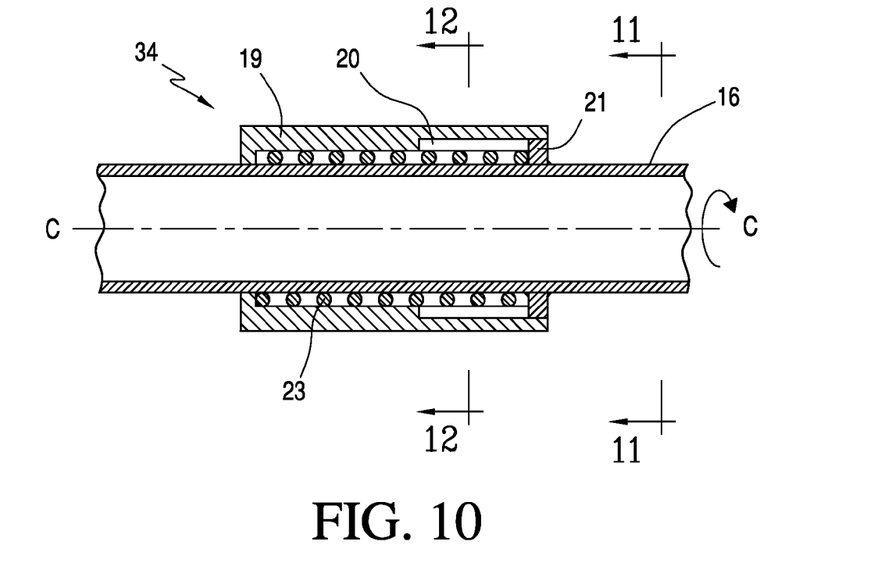
FIG. 10 is a cross-sectional view of a proximal portion of the multi-tubular cryoprobe showing a mechanical means for providing the desired actuation of the cryoprobe.
Figure 11:
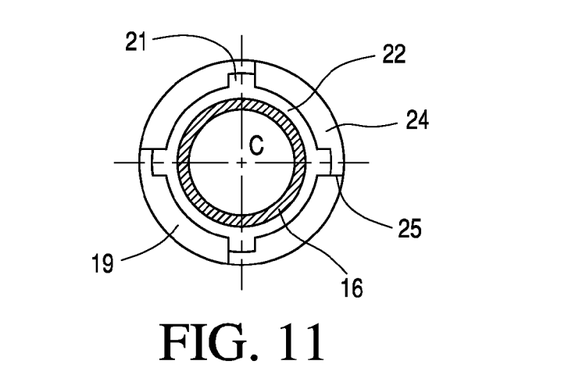
FIG. 11 is a view taken along line 11-11 of FIG. 10.
Figure 12:
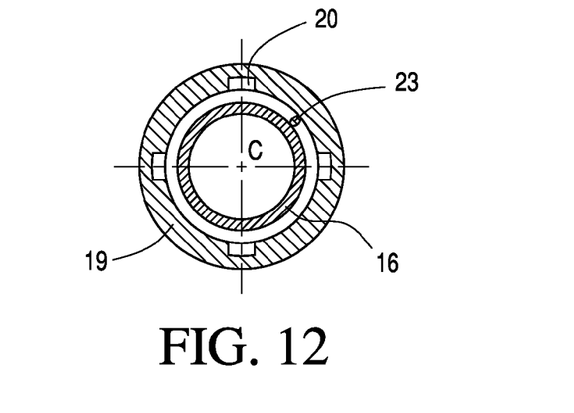
FIG. 12 is a view taken along line 12-12 of FIG. 10.

There are many mechanical means that may be utilized for providing axial displacement of the outer support tube relative to the distal external end cap, as understood by those skilled in this field. Referring to FIGS. 10-12 one possible mechanical means is illustrated, designated generally as 34.

The outlet fluid transfer tube 16 is inserted into an external cylindrical shell 19 having four axially extending linear grooves 20 that receive four protrusions 21 located on the outer surface of the ring 22. The external cylindrical shell 19 is positioned on the cryoprobe proximal to the distal end of the cryoprobe that was illustrated in FIG. 2. The ring 22 is rigidly connected to the outlet fluid transfer tube 16.

The cylindrical spiral spring 23 is placed between the inner surface of the shell 19 and outer surface of the outlet fluid transfer tube 16, so that the distal end of the spring 23 is in contact with the ring 22 and proximal end is in contact with cylindrical shell 19.

The butt-end of the shell 19 has a sloped surface divided in four equal parts forming four sliding ways for the ring 22 while rotating the ring 22 and outlet fluid transfer tube 16 around the axis C-C with a ¼ of revolution (the electrically powered drive is not shown).

The sliding ways have small ledges 25 to stop the rotation of the ring 22 shown in FIG. 10. In this position the protrusions 21 may slide within the grooves 20 in order to realize an axial displacement of the ring 22 and outlet fluid transfer tube 16 with simultaneous compression of the spiral spring 23.

The reverse movements of the ring 22 and outlet fluid transfer tube 16 may be easily accomplished.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent is:

1. A cryosurgical system, comprising:
   a) a source of near critical cryogenic fluid; and,
   b) a flexible multi-tubular cryoprobe, comprising:
      i. a housing for receiving an inlet flow of said near critical cryogenic fluid from said source of near critical cryogenic fluid and for discharging an outlet flow of said near critical cryogenic fluid;
      ii. an outer support tube connected to said housing;
      iii. a set of radially spaced inlet fluid transfer tubes having proximal ends securely attached to an inner surface of said outer support tube, said set of radially spaced inlet fluid transfer tubes for receiving said inlet flow of said near critical cryogenic fluid from said housing, each radially spaced inlet fluid transfer tube of said set of radially spaced inlet fluid transfer tubes being formed of material that maintains flexibility in a full range of temperatures from −200° C. to ambient temperature, each radially spaced inlet fluid transfer tube having an inside diameter in a range of between about 0.10 mm and 1.0 mm, each radially spaced inlet fluid transfer tube having a wall thickness in a range of between about 0.01 mm and 0.30 mm;
      iv. a proximal internal support tube included on an interior side of the set of radially spaced inlet fluid transfer tubes opposite to a side where said set of radially spaced inlet fluid transfer tubes attach to said inner surface of said outer support tube at said proximal ends of said set of radially spaced inlet fluid transfer tubes, thus forming a hollow space between said proximal internal support tube and said outer support tube to provide a thermal insulation between said outer support tube and said proximal internal support tube;
      v. an outlet fluid transfer tube positioned within said proximal internal support tube, said outlet fluid transfer tube being axially positionable and rotatable relative to said proximal internal support tube, said outlet fluid transfer tube for discharging said outlet flow to said housing;
      vi. a distal external end cap secured about distal ends of said set of radially spaced inlet fluid transfer tubes and about a distal end of said outlet fluid transfer tube to provide fluid transfer from said set of radially spaced inlet fluid transfer tubes to said outlet fluid transfer tube wherein a closed hollow space is formed between said distal external end cap and said distal end of said outlet fluid transfer tube to provide fluid transfer from said distal ends of said set of radially spaced inlet fluid transfer tubes to said distal end of said outlet fluid transfer tube;
      vii. an open portion of said set of radially spaced inlet fluid transfer tubes located between said outer support tube and said distal external end cap; and,
      viii. a means for providing axial displacement of said distal external end cap relative to said outer support tube, wherein, decreasing a distance therebetween results in radial expansion of said set of radially spaced inlet fluid transfer tubes to provide enhanced thermal contact thereof with target biological tissue to be treated at said open portion
         wherein said source of near critical cryogenic fluid is directly connected to the inlet fluid transfer tubes.

2. The cryosurgical system of claim 1, wherein said means for providing axial displacement of said distal external end cap relative to said outer support tube further provides relative rotation between said outer support tube and said distal external end cap for enhanced rigidity.

3. The cryosurgical system of claim 1, further comprising a thin outer layer positioned over said set of radially spaced inlet fluid transfer tubes.

4. The cryosurgical system of claim 1, wherein said near critical cryogenic fluid comprises nitrogen.

5. The cryosurgical system of claim 1, wherein said material that forms each of said radially spaced inlet fluid transfer tubes comprises annealed stainless steel.

6. The cryosurgical system of claim 1, wherein said material that forms each of said radially spaced inlet fluid transfer tubes comprises polyimide material.

7. The cryosurgical system of claim 1, wherein said material that forms each of said radially spaced inlet fluid transfer tubes comprises a material that maintains flexibility at a near critical nitrogen temperature.

8. A method for providing enhanced thermal contact thereof with target biological tissue to be treated, comprising the steps of:
   a) providing an expandable, flexible multi-tubular cryoprobe, comprising:
      i. a housing for receiving an inlet flow of near critical cryogenic fluid from a fluid source and for discharging an outlet flow of said near critical cryogenic fluid;
      ii. an outer support tube connected to said housing;
      iii. a set of radially spaced inlet fluid transfer tubes having proximal ends securely attached to an inner surface of said outer support tube, said set of radially spaced inlet fluid transfer tubes for receiving said inlet flow from said housing, each radially spaced inlet fluid transfer tube of said set of radially spaced inlet fluid transfer tubes being formed of material that maintains flexibility in a full range of temperatures from −200° C. to ambient temperature, each radially spaced inlet fluid transfer tube having an inside diameter in a range of between about 0.10 mm and 1.0 mm, each radially spaced inlet fluid transfer tube having a wall thickness in a range of between about 0.01 mm and 0.30 mm;

iv. a proximal internal support tube included on an interior side of the set of radially spaced inlet fluid transfer tubes opposite to a side where said set of radially spaced inlet fluid transfer tubes attach to said inner surface of said outer support tube at said proximal ends of said set of radially spaced inlet fluid transfer tubes, thus forming a hollow space between said proximal internal support tube and said outer support tube to provide a thermal insulation between said outer support tube and said proximal internal support tube;

v. an outlet fluid transfer tube positioned within said proximal internal support tube, said outlet fluid transfer tube being axially positionable and rotatable relative to said proximal internal support tube, said outlet fluid transfer tube for discharging said outlet flow to said housing;

vi. a distal external end cap secured about distal ends of said set of radially spaced inlet fluid transfer tubes and about a distal end of said outlet fluid transfer tube to provide fluid transfer from said set of radially spaced inlet fluid transfer tubes to said outlet fluid transfer tube wherein a closed hollow space is formed between said distal external end cap and said distal end of said outlet fluid transfer tube to provide fluid transfer from said distal ends of said set of radially spaced inlet fluid transfer tubes to said distal end of said outlet fluid transfer tube;

vii. an open portion of said set of radially spaced inlet fluid transfer tubes located between said outer support tube and said distal external end cap; and viii. a means for providing axial displacement of said distal external end cap relative to said outer support tube, wherein, decreasing a distance therebetween results in radial expansion of said set of radially spaced inlet fluid transfer tubes to provide enhanced thermal contact thereof with target biological tissue to be treated at said open portion; and, b) actuating said means for providing axial displacement of said distal external end cap relative to said outer support tube to decrease the distance between said outer support tube and said distal external end cap resulting in radial expansion of said inlet fluid transfer tubes to provide enhanced thermal contact thereof with the target biological tissue to be treated at said open portion wherein said source of near critical cryogenic fluid is directly connected to the inlet fluid transfer tubes.

9. The method of claim 8, further including the step of rotating said distal external end cap relative to said outer support tube for providing enhanced rigidity of each of said radially spaced inlet fluid transfer tubes.

\* \* \* \* \*